United States Patent [19]
Kume

[11] Patent Number: 5,882,290
[45] Date of Patent: Mar. 16, 1999

[54] INTRAVASCULAR RADIATION DELIVERY SYSTEM

[75] Inventor: Stewart M. Kume, Plymouth, Minn.

[73] Assignee: SCIMED Life Systems, Inc., Maple Grove, Minn.

[21] Appl. No.: 608,655

[22] Filed: Feb. 29, 1996

[51] Int. Cl.⁶ ..................................................... A61N 5/00
[52] U.S. Cl. ................................. 600/3; 606/194; 604/96
[58] Field of Search ............................ 600/1–8; 128/772; 606/194, 191; 604/96, 101, 52, 53, 264

[56] References Cited

U.S. PATENT DOCUMENTS

| | | |
|---|---|---|
| 3,324,847 | 6/1967 | Zoumboulis . |
| 3,750,653 | 8/1973 | Simon . |
| 3,811,426 | 5/1974 | Culver et al. . |
| 3,927,325 | 12/1975 | Hungate et al. . |
| 4,096,862 | 6/1978 | DeLuca . |
| 4,588,395 | 5/1986 | Lemelson . |
| 4,706,652 | 11/1987 | Horowitz . |
| 4,763,642 | 8/1988 | Horowitz . |
| 4,763,671 | 8/1988 | Goffinet . |
| 4,815,449 | 3/1989 | Horowitz . |
| 4,819,618 | 4/1989 | Liprie . |
| 4,897,076 | 1/1990 | Puthawala et al. . |
| 4,936,823 | 6/1990 | Colvin et al. . |
| 4,963,128 | 10/1990 | Daniel et al. . |
| 4,976,266 | 12/1990 | Huffman et al. . |
| 4,976,680 | 12/1990 | Hayman et al. . |
| 5,030,194 | 7/1991 | Van't Hooft et al. . |
| 5,059,166 | 10/1991 | Fischell et al. . |
| 5,084,001 | 1/1992 | Van't Hooft et al. . |
| 5,084,002 | 1/1992 | Liprie . |
| 5,092,834 | 3/1992 | Bradshaw et al. . |
| 5,106,360 | 4/1992 | Ishiwara et al. . |
| 5,139,473 | 8/1992 | Bradshaw et al. . |
| 5,141,487 | 8/1992 | Liprie . |
| 5,147,282 | 9/1992 | Kan . |
| 5,176,617 | 1/1993 | Fischell et al. . |
| 5,183,455 | 2/1993 | Hayman et al. . |
| 5,199,939 | 4/1993 | Dake et al. . |
| 5,213,561 | 5/1993 | Weinstein et al. . |
| 5,267,960 | 12/1993 | Hayman et al. . |
| 5,282,781 | 2/1994 | Liprie . |

(List continued on next page.)

FOREIGN PATENT DOCUMENTS

| | | |
|---|---|---|
| 93203354.1 | 12/1990 | European Pat. Off. . |
| 94109858.4 | 6/1994 | European Pat. Off. . |
| 0 633 041 A1 | 1/1995 | European Pat. Off. . |
| 0 593 136 B1 | 3/1997 | European Pat. Off. . |
| 9102312 | 8/1992 | Germany . |
| 92/07447 | 9/1992 | WIPO . |
| PCT/EP94/ 01373 | 4/1994 | WIPO . |
| PCT/US94/ 04857 | 5/1994 | WIPO . |
| PCT/US95/ 00826 | 1/1995 | WIPO . |
| WO 95/07732 A1 | 3/1995 | WIPO . |
| PCT/US95/ 10922 | 8/1995 | WIPO . |

OTHER PUBLICATIONS

Effect of Iridium 192 Radiation on Thromboatherosclerotic Plaque in the Rabbit Aorta, Arch Path—vol. 80, Sep. 1965.

The Antiatherogenic Effect of Iridum Upon the Cholesterolfed Rabbit, Journal of Clinical Investigation, vol. 43, No. 2, 1964.

Intravascular Irradiation of the Internal Mammary Lymph Nodes in Breast Cancer, vol. 35. No. 3.

Primary Examiner—John P. Lacyk
Attorney, Agent, or Firm—Robert E. Atkinson

[57] ABSTRACT

An intravascular catheter used to deliver radiation to a vascular wall wherein the catheter includes an elongate shaft having a toroidal-serpentine balloon connected to its distal end. The toroidal-serpentine balloon provides a non-helical perfusion path while centering a delivery lumen inside the vasculature. A guide wire and/or a radiation source may be inserted into the delivery lumen. Methods of use and manufacture are also disclosed.

18 Claims, 3 Drawing Sheets

U.S. PATENT DOCUMENTS

| | | | |
|---|---|---|---|
| 5,295,995 | 3/1994 | Kleiman | 606/194 |
| 5,302,168 | 4/1994 | Hess . | |
| 5,308,356 | 5/1994 | Blackshear, Jr. et al. | 606/194 |
| 5,354,257 | 10/1994 | Roubin et al. . | |
| 5,405,309 | 4/1995 | Carden, Jr. . | |
| 5,411,466 | 5/1995 | Hess . | |
| 5,425,720 | 6/1995 | Rogalsky et al. . | |
| 5,429,582 | 7/1995 | Williams . | |
| 5,484,384 | 1/1996 | Fearnot . | |
| 5,498,227 | 3/1996 | Mawad . | |
| 5,503,613 | 4/1996 | Weinberger . | |
| 5,503,614 | 4/1996 | Liprie . | |
| 5,538,494 | 7/1996 | Matsuda . | |
| 5,540,659 | 7/1996 | Teirstein | 604/53 |
| 5,545,132 | 8/1996 | Fagan et al. | 606/194 |
| 5,575,749 | 11/1996 | Liprie . | |
| 5,616,114 | 4/1997 | Thornton et al. . | |
| 5,618,266 | 4/1997 | Liprie . | |
| 5,624,372 | 4/1997 | Liprie . | |
| 5,643,171 | 7/1997 | Bradshaw . | |
| 5,649,924 | 7/1997 | Everett et al. . | |
| 5,653,683 | 8/1997 | D'Andrea . | |
| 5,662,580 | 9/1997 | Bradshaw et al. . | |
| 5,683,345 | 11/1997 | Waksman et al. . | |
| 5,688,220 | 11/1997 | Verin et al. . | |
| 5,707,332 | 1/1998 | Weinberger . | |
| 5,720,717 | 2/1998 | D'Andrea . | |
| 5,722,984 | 3/1998 | Fischell et al. . | |
| 5,730,698 | 3/1998 | Fischell et al. . | |

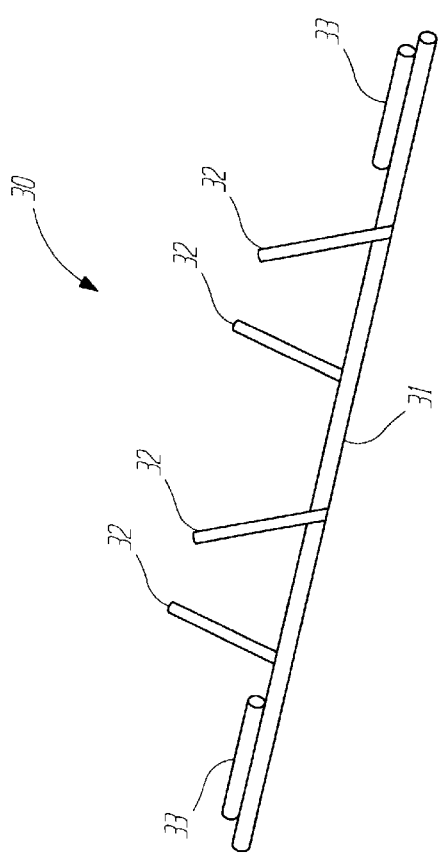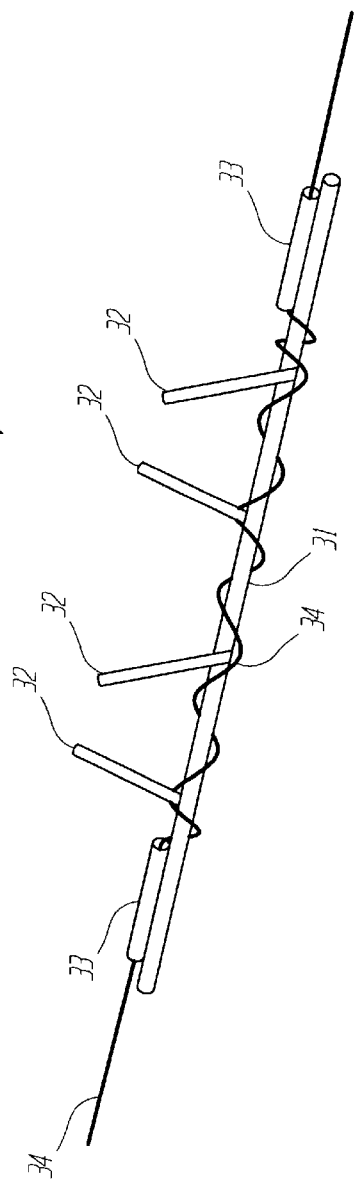

INTRAVASCULAR RADIATION DELIVERY SYSTEM

FIELD OF THE INVENTION

The present invention generally relates to intralumenal devices used to deliver radiation inside a living body. More specifically, the present invention relates to intravascular devices used to deliver radiation inside the vasculature of a patient for therapeutic purposes. Those skilled in the art will recognize the benefits of applying the present invention to similar fields not discussed herein.

BACKGROUND OF THE INVENTION

Intravascular diseases are commonly treated by relatively non-invasive techniques such as percutaneous transluminal angioplasty (PTA) and percutaneous transluminal coronary angioplasty (PTCA). These therapeutic techniques are well-known in the art and typically involve the use of a balloon catheter with a guide wire, possibly in combination with other intravascular devices. A typical balloon catheter has an elongate shaft with a balloon attached to its distal end and a manifold attached to the proximal end. In use, the balloon catheter is advanced over the guide wire such that the balloon is positioned adjacent a restriction in a diseased vessel. The balloon is then inflated and the restriction in the vessel is opened.

Vascular restrictions that have been dilated do not always remain open. For example, the restriction may redevelop over a period of time, a phenomenon commonly referred to as restenosis. Various theories have been developed to explain the cause for restenosis. It is commonly believed that restenosis is caused, at least in part, by cellular proliferation over a period of time to such a degree that a stenosis or restriction is reformed in the location of the previously dilated restriction.

Intravascular radiation, including thermal, light and radioactive radiation, has been proposed as a means to prevent or reduce the effects of restenosis. For example, U.S. Pat. No. 4,799,479 to Spears suggests that heating a dilated restriction may prevent gradual restenosis at the dilation site. In addition, U.S. Pat. No. 5,417,653 to Sahota et al. suggests that delivering relatively low energy light, following dictation of a stenosis, may inhibit restenosis. Furthermore, U.S. Pat. No. 5,059,166 to Fischell et al. suggests that intravascular delivery of radioisotopes may be used to decrease the rate of arterial reclosure (i.e., restenosis).

Since the delivery of intravascular radiation may adversely affect otherwise healthy tissue, it is desirable to limit radiation exposure to areas requiring treatment. In addition, it is desirable to uniformly deliver radiation to the treatment site in order to avoid over-exposing some areas and underexposing other areas. Since the human vasculature is rarely linear, it is further desirable to provide for uniform distribution of radiation along vascular paths that are non-linear (i.e., curved). Accordingly, it is desirable to center the radiation source within the vasculature, including linear sections and non-linear sections, in order to uniformly irradiate the surrounding tissue. It is also desirable to maintain patency (i.e., retain a fluid path) across the treatment site while delivering radiation over a prolonged period of time. As such, it is desirable to provide structural support to the vessel at the treatment site while permitting blood perfusion.

Although some prior art references recognize these desirable aspects, the prior art does not disclose a device nor method for providing all of these desirable features in a single, functional and effective device. For example, U.S. Pat. No. 5,484,384 to Fearnot discloses a perfusion balloon catheter that has a central lumen for delivering radiation. However, this device will not adequately center the radiation source if the vasculature is tortuous or otherwise non-linear. Another example is disclosed in European Patent No. 0 688 580 A1 to Verin wherein a device is provided which includes a central radiation delivery lumen that remains centered in both linear and non-linear vessels. However, this device does not provide a means for blood perfusion.

SUMMARY OF THE INVENTION

The present invention provides a device and method providing all the desirable aspects outlined above in a functional, feasible and effective manner. In particular, the present invention provides for uniform delivery of radiation in linear and non-linear vascular paths, structural support for the vessel at the treatment site and simultaneously permits blood perfusion.

The present invention may be described as an intravascular catheter used to deliver radiation to a vascular wall wherein the catheter includes an elongate shaft having a toroidal-serpentine balloon connected to the distal end of the shaft. The elongate shaft includes an inflation lumen for inflating the toroidal-serpentine balloon and a delivery lumen in which a guide wire and/or a radiation source may be inserted. The delivery lumen may have an open end or a closed end. A portion of the shaft may extend through the center of the toroidal-serpentine balloon such that a radiation source inserted therein will be centered in both linear and non-linear vasculature and uniformly deliver radiation to the vessel wall. The toroidal-serpentine balloon may define a perfusion path when the balloon is inflated between the vascular wall and the portion of the shaft that extends through the toroidal-serpentine balloon. The perfusion path defined by the toroidal-serpentine balloon is non-helical and may be, for example, linear or serpentine.

The present invention may also be described as a method of delivering radiation to a vascular wall of a patient wherein the method includes the steps of (1) providing a radiation delivery catheter substantially as described above, (2) inserting the delivery catheter into the vasculature of the patient, (3) inserting a radiation source (which may include a closed-end sheath for safety, handling and/or sterility purposes) into the delivery lumen of the catheter such that the radiation source is positioned along the central axis of the toroidal-serpentine balloon, (4) inflating the balloon, (5) exposing the vascular wall to radiation from the radiation source, (6) removing the radiation source from the patient, and (7) removing the delivery catheter from the patient. The delivery catheter may be inserted into the vasculature over a guide wire in which case the guide wire may remain in place across the treatment site, the guide wire may be partially retracted in the proximal direction or the guide wire may be fully removed from the delivery catheter prior to exposing the vascular wall to radiation. After treating the vascular wall, the radiation source and the delivery catheter may be removed individually or at the same time.

BRIEF DESCRIPTION OF THE DRAWINGS

FIG. 6a is a perspective view of a balloon-forming fixture which may be used to manufacture a toroidal-serpentine balloon and FIG. 6b illustrates the balloon-forming fixture with a parison loaded thereon.

DETAILED DESCRIPTION OF THE INVENTION

The following detailed description should be read with reference to the drawings in which similar parts in different drawings are numbered the same. The drawings, which are not necessarily to scale, depict exemplary embodiments and are not intended to limit the scope of the invention.

Examples of materials, dimensions, assemblies and manufacturing processes are provided for selected parts. All other parts employ that which is known to those skilled in the field of the invention. Those skilled in the field will recognize that many of the examples provided have suitable alternatives which may also be utilized.

Figure 1:
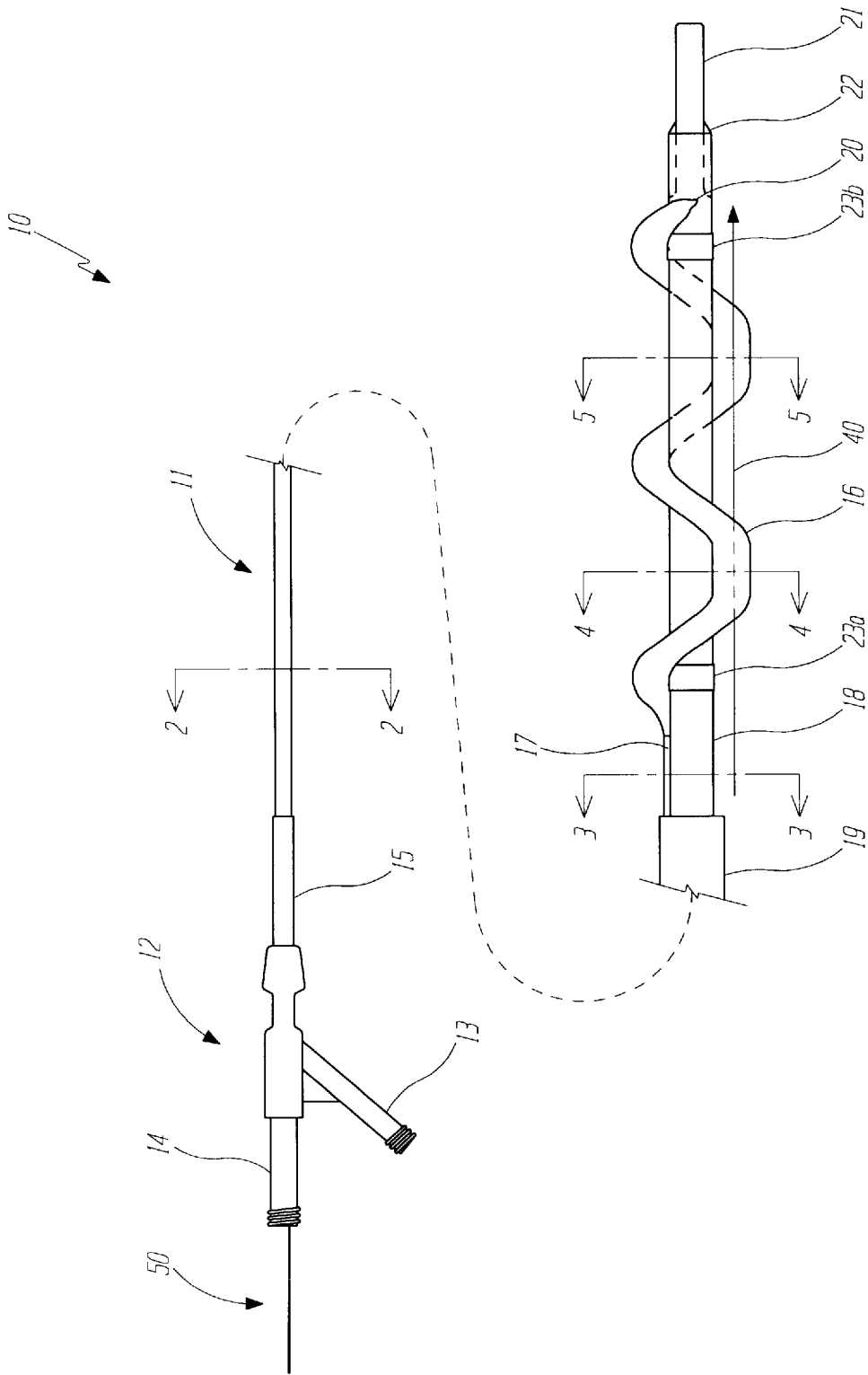
FIG. 1 is a side view of a radiation delivery catheter of the present invention.

Refer now to FIG. 1 which illustrates a radiation delivery catheter 10 of the present invention. Radiation delivery catheter 10 includes an elongate shaft 11 having a manifold 12 connected to its proximal end. Manifold 12 includes an inflation port 13 and a delivery port 14. Inflation port 13 provides a means to connect an inflation device for inflating the balloon 16 via the inflation lumen 24. Delivery port 14 provides access for a guide wire (not shown) and/or a radiation source 50 to be inserted into the delivery lumen 25. (Note: The radiation source 50 may include a closed-end sheath 51 that is also insertable into the delivery lumen). A strain relief 15 may be secured to the manifold 12 and/or the shaft 11 to reduce the tendency of the shaft 11 to kink immediately adjacent the distal end of the manifold 12.

Figure 3:
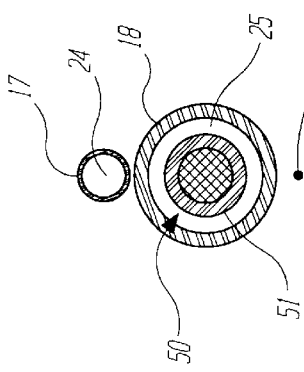
FIGS. 2, 3, 4 and 5 are cross-sectional views of the delivery catheter taken at sections 2—2, 3—3, 4—4 and 5—5 in FIG. 1, respectively.
Figure 2:
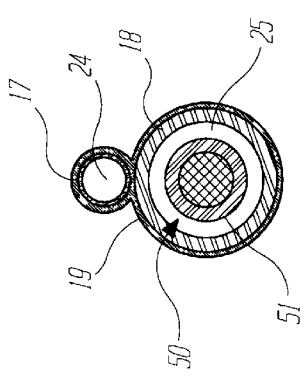

Shaft 11 includes delivery tube 18 and inflation tube 17 secured together in a side-by-side parallel relationship with sheath 19, as best shown in FIGS. 2 and 3. The proximal end of the inflation tube 17 is connected to the inflation port 13 of the manifold 12 and the distal end of the inflation tube 17 is connected to the proximal end of the toroidal-serpentine balloon 16. The balloon 16 is wrapped about the circumference of the delivery tube 18 in a serpentine pattern to form a toroidal-serpentine geometry. (Note: A more elegant illustration of this general geometry is disclosed in FIG. 1 of U.S. Pat. No. 4,907,336 to Gianturco.) A thin polymer coating may be used to secure the body of the balloon 16 to the delivery tube 18 and retain the toroidal-serpentine geometry of the balloon 16. Alternatively, an adhesive may be used to secure the balloon 16 to the delivery tube 18. The distal end of the balloon 16 is fluidly sealed and tucked inside delivery tube 18 via hole 20.

The portion of the delivery tube 18 that traverses the inside of the balloon 16 is automatically centered inside the vasculature when the balloon 16 is inflated to come into contact with the inside wall of the vessel. (Note: The term "wall" refers to the inside surface of the vessel whether the inside surface comprises native tissue, abnormal deposits or a combination thereof.) Since the lateral moment of inertia of the toroidal-serpentine balloon 16 is relatively small compared to a conventional cylindrical balloon having the same outside profile, the balloon 16 is able to bend in the same geometry as the vessel. As such, the balloon 16 and the portion of the delivery tube 18 traversing the balloon 16 are able to remain centered inside both linear and non-linear portions of the vasculature.

Figure 5:
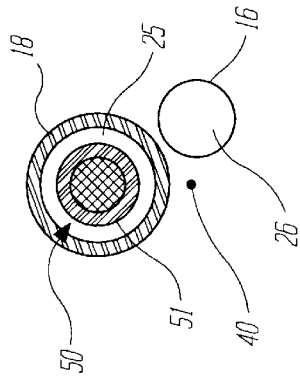
Figure 4:
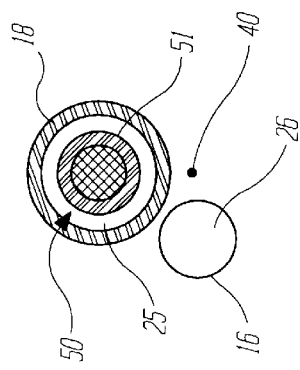

The toroidal-serpentine balloon 16 structure defines a perfusion path 40 between the outer surface of the delivery tube 18 and the inside surface of the vessel wall. Given this geometry, the perfusion path is either linear or serpentine and is not helical. The perfusion path is non-helical because the path never makes a full rotation around the delivery tube 18. Whether the balloon 16 defines a linear or serpentine path is dictated by the extent of angular overlap between adjacent apexes. For example, as best seen in Figures 4 and 5, a linear path 40 is defined when adjacent apexes do not overlap the same angular coordinate. A serpentine path is defined when adjacent apexes do overlap the same angular coordinate and the degree of serpentine curvature in the perfusion path increases with the degree of angular overlap. It is believed that a non-helical (e.g., linear or serpentine) perfusion path is desirable because it minimizes drag on blood flow resulting in improved perfusion. In addition, the non-helical path minimizes the rotational momentum of blood flow.

An atraumatic tip 21 is secured to the distal end of the delivery tube 18 and provides for atraumatic navigation through the vascular system. Atraumatic tip 21 has an inside diameter that is large enough to permit passage of a guide wire, but small enough to prohibit passage of a radiation source. The proximal end of the tip 21 which extends partially inside the distal end of the delivery tube 18 is preferably flared to provide a smooth transition from the interior wall of the delivery tube 18 to the interior of the tip 21. The transition from the outside surface of the distal end of the delivery tube 18 to the outside surface of the atraumatic tip 21 preferably includes a taper 22. The distal end of the atraumatic tip 21 is formed into a tapered blunt end in order to facilitate atraumatic navigation and the ability to cross tight restrictions.

Proximal marker band 23a and distal marker band 23b are connected to the delivery tube 18 adjacent the proximal and distal ends of the balloon, respectively. Marker bands 23a and 23b are made of a radiopaque material and are visible in-vivo using conventional radiographic techniques. Marker bands 23a and 23b facilitate proper placement of the balloon 16 section at the desired treatment site.

The overall length and profile of the delivery catheter 10 is dictated in part by the anatomy in which the catheter will be inserted and further dictated by the size of the radiation source to be inserted into the delivery lumen 25. For peripheral vascular applications, the overall length of the catheter 10 may be about 75 to 120 cm with an outside profile of about 4F to 8F. The inflatable balloon segment may be approximately 5 to 15 cm in length having an inflated outer profile of about 3.0 mm to 12.0 mm. Those skilled in the art will recognize that these dimensions may be varied depending on the particular vasculature to be navigated, the vascular site to be treated and the size of the radiation source.

Manifold 12 and strain relief 15 may be manufactured and assembled using conventional materials, dimensions and processes. The manifold 12 may be secured to the proximal end of the shaft 11 using conventional bonding techniques such as thermal bonding and the use of medical grade adhesives.

Elongate shaft 11 includes an inflation tube 17 arranged in a side-by-side parallel relationship with delivery tube 18 and held together by sheath 19. The shaft 11 may be a composite structure as shown or an integral structure such as a multi-lumen extrusion. Although the examples discussed herein are with reference to a composite structure, those skilled in the art will recognize that other shaft constructions may be employed.

It is contemplated that additional lumens may be provided to accommodate different adjunct devices or different methods of use. For example, the shaft 11 may include an additional lumen to accommodate a guide wire so that the radiation source and the guide wire need not share the same lumen. Accordingly, the guide wire does not need to be retracted or removed in order to insert the radiation source. This would permit the treating physician to retain guide wire access across the treatment site or merely retract the guide wire during radiation exposure. If a separate guide wire lumen were provided, the delivery lumen 25 may remain centered by placing the guide wire lumen adjacent to the delivery tube 18 and constructing the balloon 16 with an inside recess to accommodate the guide wire lumen. Alternatively, the guide wire may run adjacent the delivery tube 18 through the perfusion path. It is also contemplated that the guide wire lumen may be full length to allow for simple guide wire exchanges or part length (i.e., distal section only) to allow for single operator catheter 10 exchanges.

As mentioned previously, the radiation source may include a closed-end sheath for safety, handling and/or sterility purposes. In a similar manner, the delivery tube 18 may have a closed distal end such that the delivery lumen 25 is closed distally and open proximally. A guide wire may still be used with a closed-end delivery tube 18 construction if a separate guide wire lumen is provided as described above.

With reference now to the composite shaft 11 embodiment, inflation tube 17 may be formed of polyimide having a wall thickness of approximately 0.001 inches and an inside diameter ranging from about 0.010 to 0.020 inches, depending on the desired inflation/deflation time of the balloon 16 versus the desired overall profile of the shaft 11. Delivery tube 18 may be formed of a composite structure similar to that used in guide catheters and diagnostic catheters. For example, delivery tube 18 may be a composite structure including a PTFE inner layer, a coaxial layer of stainless steel braid surrounded by a coaxial layer of polyether-block-amide. Delivery tube 18 may have an inside diameter of about 0.074 inches and an outside diameter of about 0.092 inches, depending in part on the size of the radiation source to be inserted therein. Sheath 19 may be made of a heat-shrinkable tube such as an extruded polyolefin tube that has been irradiated and free-blown.

Tip 21 may be made of an extruded polymer tube, a molded tip, or an integral continuation of the delivery tube 18 modified by interrupted extrusion. Tip 21 has an inside diameter which is sufficiently large to permit passage of the guide wire but sufficiently small to prevent passage of the particular radiation source employed. For example, tip 21 may have an inside diameter of approximately 0.038 inches, an outside diameter of approximately 0.072 inches and a length of approximately 1.0 inch. The proximal end of the tip 21 may be flared by thermal forming means to provide a smooth transition from the interior surface of the delivery tube 18 to the interior surface of the tip 21. The transition from the outside surface of the distal end of the delivery tube 18 to the outside surface of the atraumatic tip 21 may be tapered by utilizing an adhesive 22 such as urethane. The distal end of the atraumatic tip 21 may be tapered by thermal forming or grinding.

Radiopaque marker bands 23a and 23b may be formed of a radiopaque material such as a platinum iridium alloy in the form of a solid tube or a coiled wire.

Referring to FIGS. 6a and 6b, toroidal-serpentine balloon 16 may be formed by utilizing fixture 30 to free blow a polymer extrusion. An example of a suitable polymer is a polyelefin polymer sold under the trade name Surlyn® Ionomer from E. I. Dupont. Preferably, this polyolefin polymer is irradiated to cross-link the material. The outside diameter of the balloon 16 may range from about 1.0 mm to 5.0 mm and the outside profile of the toroidal-serpentine structure may range from about 3 mm to 12 mm, both depending on the size of the vessel being treated. At least one full serpentine section (one section=apex to adjacent apex) is required to center the delivery tube 18. About 5 to 15 sections may be used to provide an adequate working section and each section may be about 0.5 to 1.5 cm in length.

To form the toroidal-serpentine geometry utilizing fixture 30, the parison (e.g., irradiated polyolefin extruded tube) is fed through a guide 33, wound in a clockwise direction around the backbone 31, wrapped around the outside of a rib 32, wound in a counterclockwise direction around the backbone 31, wrapped around the outside of an adjacent and opposite rib 32, etc., until the desired number of sections are mounted on the fixture 30. One end of the parison is sealed (e.g., with a clamp) and the other end is connected to a pressurized fluid source. The fixture 30, with the parison mounted thereon, is exposed to heat and the parison is pressurized to cause it to inflate. Once inflated, the parison is cooled, removed from the fixture, trimmed to length and mounted of the shaft 11 of the delivery catheter 10. The body of the toroidal-serpentine balloon 16 may be secured to delivery tube 18 utilizing an adhesive or a polymer coating. For example, a polymer coating may be applied by dip-coating the assembly in a solution of urethane such as 14% Pellethane 2363-80AE (available from Dow Plastics), 77.4% tetrahydrofuran and 8.6% dimethlacetamide. The proximal and distal ends of the balloon 16 may be sealingly secured using a suitable medical grade adhesive.

In use, the radiation delivery catheter 10 is first inserted into the vasculature of a patient. The catheter 10 may be inserted over a pre-inserted guide wire, along with a guide wire, or without a guide wire. Once the balloon 16 is correctly positioned as determined radiographically utilizing marker bands 23a and 23b, a radiation source is inserted into the delivery lumen of the catheter such that the radiation source is positioned inside the toroidal-serpentine balloon 16. Prior to inserting the radiation source, the guide wire may need to be removed from the delivery lumen 25. In addition, it may be preferable to inflate the balloon 16 prior to inserting the radiation source. Once in position and after the balloon is inflated, the vascular wall may be exposed to radiation from the radiation source. After the therapy is complete, the radiation source and the delivery catheter 10 are removed from the patient either together or independently.

While the specification describes the preferred embodiments, those skilled in the art will appreciate the spirit and scope of the invention with reference to the appended claims.

What is claimed is:

1. An intravascular catheter used to deliver radiation to a vascular wall, comprising:
   a. an elongate shaft having a proximal end, a distal end, an inflation lumen and a delivery lumen; and
   b. a toroidal-serpentine balloon connected to the distal end of the elongate shaft, the balloon fluidly communicating with the inflation lumen.

2. A catheter as in claim 1 wherein the elongate shaft includes a separate guide wire lumen.

3. A catheter as in claim 1 wherein a portion of the elongate shaft traverses along a central axis of the toroidal-serpentine balloon.

4. A catheter as in claim 3 wherein a perfusion path is defined by the toroidal-serpentine balloon between the vascular wall and the portion of the elongate shaft that traverses along the central axis of the toroidal-serpentine balloon.

5. An intravascular catheter used to deliver radiation to a vascular wall, comprising:
   a. an elongate shaft having a proximal end, a distal end, an inflation lumen and a delivery lumen;
   b. a toroidal-serpentine balloon connected to the distal end of the elongate shaft such that a portion of the elongate shaft traverses along a central axis of the toroidal-serpentine balloon, the balloon fluidly communicating with the inflation lumen; and
   c. a non-helical perfusion path defined by the toroidal-serpentine balloon between the vascular wall and the portion of the elongate shaft that traverses along the central axis of the toroidal-serpentine balloon.

6. A method of delivering radiation to a vascular wall of a patient, comprising the steps of:
   a. providing a radiation delivery catheter comprising:
      i. an elongate shaft having a proximal end, a distal end, an inflation lumen and a delivery lumen;
      ii. a toroidal-serpentine balloon connected to the distal end of the elongate shaft such that a portion of the elongate shaft traverses along a central axis of the toroidal-serpentine balloon, the balloon fluidly communicating with the inflation lumen; and
      iii. a non-helical perfusion path defined by the toroidal-serpentine balloon between the vascular wall and the portion of the elongate shaft that traverses along the central axis of the toroidal-serpentine balloon;
   b. inserting the delivery catheter into the vasculature;
   c. inserting a radiation source into the delivery lumen such that the radiation source is positioned in the portion of the elongate shaft that traverses along the central axis of the toroidal-serpentine balloon;
   d. inflating the toroidal-serpentine balloon;
   e. exposing the vascular wall to radiation from the radiation source;
   f. removing the radiation source from the patient; and
   g. removing the delivery catheter from the patient.

7. A method of delivering radiation to a vascular wall of a patient as in claim 6, wherein the delivery catheter is inserted into the vasculature over a guide wire.

8. A method of delivering radiation to a vascular wall of a patient as in claim 7, wherein the guide wire is retracted prior to exposing the vascular wall to radiation.

9. A method of delivering radiation to a vascular wall of a patient as in claim 8, wherein the guide wire is removed from the delivery catheter prior to exposing the vascular wall to radiation.

10. A method of delivering radiation to a vascular wall of a patient as in claim 6, wherein the radiation source and the delivery catheter are removed from the patient at the same time.

11. A method of delivering radiation to a vascular wall of a patient, comprising the steps of:
   a. providing a balloon catheter, the balloon catheter including an elongate shaft having an inflation lumen and a delivery lumen, the delivery lumen having an open distal end;
   b. providing a radiation source, the radiation source including a closed-end sheath;
   c. inserting the balloon catheter into the vasculature;
   d. inserting the radiation source into the delivery lumen;
   e. inflating the balloon;
   f. exposing the vascular wall to radiation from the radiation source;
   g. removing the radiation source from the patient; and
   h. removing the balloon catheter from the patient.

12. A method of delivering radiation to a vascular wall of a patient as in claim 11, wherein the balloon catheter is inserted into the vasculature over a guide wire.

13. A method of delivering radiation to a vascular wall of a patient as in claim 12, wherein the guide wire is retracted prior to exposing the vascular wall to radiation.

14. A method of delivering radiation to a vascular wall of a patient as in claim 13, wherein the guide wire is removed from the balloon catheter prior to exposing the vascular wall to radiation.

15. A method of delivering radiation to a vascular wall of a patient as in claim 11, wherein the radiation source and the balloon catheter are removed from the patient at the same time.

16. An intravascular catheter used to deliver a radiation source to a vascular wall, comprising:
   a. an elongate shaft having a proximal end, a distal end, an inflation lumen and a delivery lumen, the delivery lumen adapted to accommodate the radiation source;
   b. a balloon connected to and wrapped around the distal end of the elongate shaft, the balloon fluidly communicating with the inflation lumen, the balloon having a geometry adapted to conform to non-linear vasculature such that the shaft remains centered in non-linear vasculature; and
   c. a substantially linear perfusion path defined by the balloon between the vascular wall and the distal end of the elongate shaft surrounded by the balloon.

17. A catheter as in claim 16 wherein the elongate shaft includes a separate guide wire lumen.

18. A method of delivering radiation to a vascular wall of a patient, comprising the steps of:
   a. providing a radiation delivery catheter comprising an elongate shaft having a proximal end, a distal end, an inflation lumen and a delivery lumen; a toroidal-serpentine shaped balloon connected to and wrapped around the distal end of the elongate shaft, the balloon fluidly communicating with the inflation lumen; and a substantially linear perfusion path defined by the balloon between the vascular wall and the distal end of the elongate shaft surrounded by the balloon;
   b. inserting the delivery catheter into the vasculature;
   c. inserting a radiation source into the delivery lumen such that the radiation source is positioned in the portion of the elongate shaft that traverses along the central axis of the toroidal-serpentine balloon;
   d. inflating the toroidal-serpentine balloon;
   e. exposing the vascular wall to radiation from the radiation source;
   f. removing the radiation source from the patient; and
   g. removing the delivery catheter from the patient.

* * * * *